United States Patent [19]

Anderson et al.

[11] E Re. 29,084

[45] Reissued Dec. 21, 1976

[54] SEPARATE RECYCLE OF REGENERATED ACID AND OF ISOPARAFFIN FROM HF CATALYST REGENERATION ZONE

[75] Inventors: Robert F. Anderson, La Grange Park; Bipin V. Vora, Wheeling, both of Ill.

[73] Assignee: Universal Oil Products Company, Des Plaines, Ill.

[22] Filed: Jan. 30, 1976

[21] Appl. No.: 653,683

Related U.S. Patent Documents

Reissue of:

[64] Patent No.: 3,879,488
Issued: Apr. 22, 1975
Appl. No.: 461,761
Filed: Apr. 17, 1974

[52] U.S. Cl. ..... 260/683.41; 260/683.48

[51] Int. Cl.[2] ..... C07C 3/54

[58] Field of Search ..... 260/683.48, 683.41, 260/683.42

[56] References Cited

UNITED STATES PATENTS

| | | | |
|---|---|---|---|
| 2,400,386 | 5/1946 | Bolinger et al. | 260/683.48 |
| 2,536,514 | 1/1951 | Penick | 260/683.48 |
| 2,632,031 | 3/1953 | Matuszak | 260/683.48 |
| 3,223,749 | 12/1965 | Van Pool et al. | 260/683.42 |
| 3,410,750 | 11/1968 | Fontenot et al. | 260/683.48 |
| 3,721,720 | 3/1973 | Chapman et al. | 260/683.48 |
| 3,749,753 | 7/1973 | Skraba | 260/683.48 |
| 3,767,726 | 10/1973 | Hutson, Jr. et al. | 260/683.42 |
| 3,793,264 | 2/1974 | Chapman | 260/683.48 |
| 3,806,588 | 4/1974 | Hann | 260/683.41 |
| 3,879,487 | 4/1975 | Vora | 260/683.48 |
| 3,937,749 | 2/1976 | Zabransky | 260/683.48 |

*Primary Examiner*—George Crasanakis
*Attorney, Agent, or Firm*—James R. Hoatson, Jr.; Robert W. Erickson; William H. Page, II

[57] ABSTRACT

An improved process for the hydrogen fluoride catalyzed alkylation of isoparaffins with olefins wherein better utilization of internal streams is achieved. Isoparaffins used as a stripping medium in the catalyst regeneration zone are reclaimed, free of a hydrogen fluoride phase, and are utilized as recycle isoparaffins to improve the quality of the alkylate product.

2 Claims, 2 Drawing Figures

SEPARATE RECYCLE OF REGENERATED ACID AND OF ISOPARAFFIN FROM HF CATALYST REGENERATION ZONE

Matter enclosed in heavy brackets [ ] appears in the original patent but forms no part of this reissue specification; matter printed in italics indicates the additions made by reissue.

BACKGROUND OF THE INVENTION

1. Field of the Invention

The field of art to which this invention pertains is hydrocarbon processing. It particularly relates to an improved process for the production of an isoparaffin-olefin alkylation product through hydrogen fluoride catalysis.

2. Prior Art

The production of higher molecular weight isoparaffins, haing valuable antiknock properties as motor fuel, is of considerable importance in the petroleum refining industry. Furthermore, the growth of the synthetic fibers and plastics industries has increased consumption of aromatic hydocarbons such that less are available for use as high octane motor fuel blending components. Thus, a demand for higher molecular weight isoparaffins as blending agents for fuels has materialized. Accompanying this demand for higher octane blending components is a demand for greater quantities of the blending components themselves due to the incessant increase in world gasoline consumption.

A convenient source of such higher molecular weight isoparaffins is the catalytic alkylation of lower boiling isoparaffinic hydrocarbons, such as isobutane, with olefinic hydrocarbons, such as propene and butenes. It is well known in the art that catalytic alkylation using acid catalysts, such as hydrofluoric acid, has become an important tool for preparing alkylated hydrocarbons. However, there is an inherent feature of conventional designs of hydrogen fluoride-catalyzed alkylation process units which contributes to poor use of internal streams. Unreacted isoparaffins leaving the reaction zone of an alkylation process are recycled and mixed with fresh feed to provide, within the reaction zone, an excess of isoparaffinic components. Isoparaffins which are thusly recycled are referred to as recycle isoparaffins. In order to beneficially affect the product quality, the recycle isoparaffins must be thoroughly mixed with other feed components such as fresh isoparaffins and fresh olefins before contact with the catalyst phase occurs. Due to the design of conventional alkylation process units the isoparaffins exiting the catalyst regeneration zone contain hydrogen fluoride as a separate phase, and this hydrogen fluoride phase can catalyze undesirable reactions which would occur upon mixing of fresh olefins with the isoparaffins. These undesirable reactions would produce contaminants which would remain in the final alkylate product and lower its quality. For this reason these regeneration zone isoparaffins are not recycled to mix with fresh feed, and their utility as recycle isoparaffins is lost. Our invention solves this prior art problem by eliminating the hydrogen fluoride phase from the regeneration zone isoparaffins and utilizing them as recycle isoparaffins.

BRIEF SUMMARY OF THE INVENTION

Our invention involves an improved hydrogen fluoride alkylation process and an improved method of regenerating the contaminated catalyst therein. Isoparaffins injected into the catalyst regeneration zone of the process of my invention are separated from regenerated catalyst and recovered for use as recycle isoparaffins. These recovered isoparaffins are free from a hydrogen fluoride phase. The isoparaffins then mix with fresh feed to the alkylation process, thereby raising the isoparaffin/olefin ratio of the feed and increasing the production of alkylate of the desirable mono-alkylate type.

OBJECTS AND EMBODIMENTS

It is an object of this invention to provide an improved process for the hydrogen fluoride catalyzed alkylation of an isoparaffin with an olefin. A still further object of our invention is to provide an improved method for regenerating the contaminated hydrogen fluoride catalyst in an isoparaffin-olefin alkylation process. Another object of the present invention is to provide a method of increasing the efficacy of existing hydrogen fluoride-catalyzed process units for production of monoalkylate.

In one embodiment our invention affords, in an alkylation process wherein (a) a feed comprising an olefin-acting hydrocarbon and an alkylatable hydrocarbon is contacted with hydrogen fluoride alkylation catalyst at alkylation reaction conditions in a reaction zone; (b) a reaction zone effluent is separated into a hydrocarbon phase and a catalyst phase; (c) a first portion of said catalyst phase is returned to said reaction zone; (d) a second portion of said catalyst phase is passed to a catalyst regeneration zone; (e) a first stream comprising regenerated catalyst and unreacted alkylatable hydrocarbon is withdrawn from said catalyst regeneration zone and mixed with said first portion of said catalyst phase prior to the introduction thereof into said reaction zone; (f) said hydrocarbon phase is passed into a separation zone; (g) a second stream comprising unreacted alkylatable hydrocarbon is withdrawn from said separation zone and mixed with said feed prior to its introduction into said reaction zone; and (h) an alkylate product is withdrawn from said separation zone; the improvement which comprises separating said first stream comprising regenerated catalyst and unreacted alkylatable hydrocarbon into a third stream comprising regenerated catalyst and a fourth stream comprising unreacted alkylatable hydrocarbon, mixing said third stream with said portion of said catalyst phase before the return thereof to said reaction zone and mixing said fourth stream with said feed prior to its introduction into said reaction zone.

BRIEF DESCRIPTION OF THE DRAWINGS

The attached drawings illustrate a particular embodiment of the present invention. Only such details are included as necessary for a clear understanding of our invention, and no intention is thereby made to unduly limit its scope. Certain items necessary to the operation of the process of this invention but unnecessary to its understanding, such as certain process streams, valves pumps, instrumentation and other equipment, have been omitted for the sake of clarity.

Referring now to FIG. 1, an alkylation feed stream enters the process of this invention in conduit 1 and is premixed therein with recycle isoparaffin from conduit 2. This feed-recycle isoparaffin admixture then passes to reaction zone 4 where contact is effected with an acid catalyst. Reaction zone effluent including acid catalyst alkylated hydrocarbons and unreacted hydrocarbons, exits the reaction zone in conduit 5 and passes to mixing-settling zone 6, where mixing and further reaction take place, and, subsequently, the reaction zone effluent is settled and separated into an acid phase and a hydrocarbon phase. The acid phase leaves mixing-settling zone 6 in conduit 15 and is divided into a portion which passes to catalyst regeneration zone 18 in conduit 17 and the remaining portion which exits conduit 15 in line 3 and passes to reaction zone 4. The hydrocarbon phase from mixing-settling zone 6 exits in conduit 7 and passes to separation zone 8.

Figure 1:
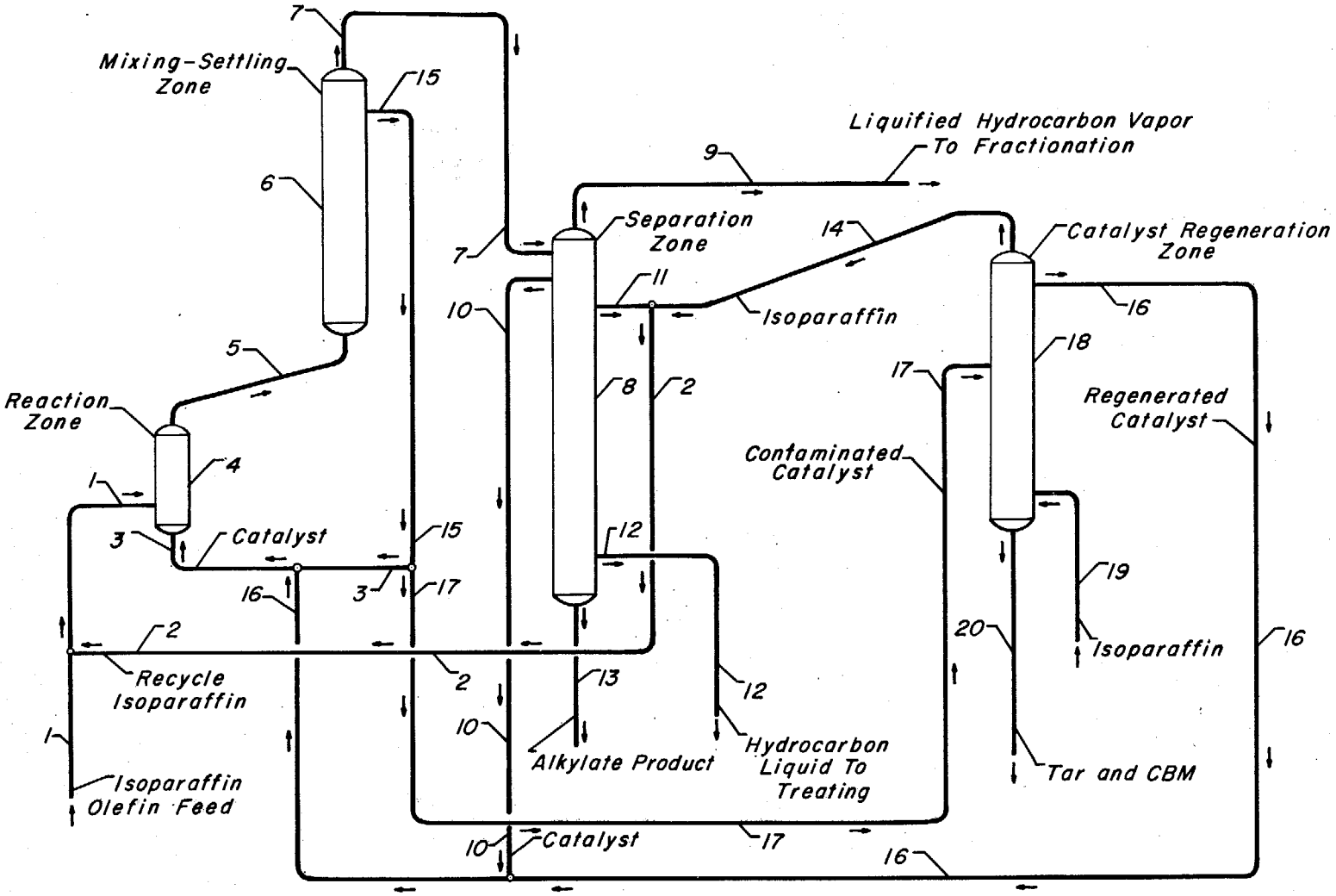
FIG. 1 is a schematic representation of a hydrogen fluoride alkylation process, having reaction zone 4 and catalyst regeneration zone 18.

Separation zone 8 is operated at conditions selected to provide an alkylate product stream, a hydrocarbon liquid stream, a liquefied hydrocarbon vapor stream, a hydrogen fluoride stream and a recycle isoparaffin stream. The alkylate product stream exits separation zone 8 in conduit 13. The hydrocarbon liquid leaves separation zone 8 in conduit 12. The recycle isoparaffins exit separation zone 8 in conduit 11, passing to conduit 2 and intermixing with isoparaffin-olefin feed to the reaction zone in conduit 1. The hydrogen fluoride streams exits separation zone 8 in conduit 10 and returns to reaction zone 4 by passing through conduits 16 and 3. The liquefied hydrocarbon vapor stream exits the separation zone in conduit 9.

A portion of the acid catalyst phase leaving mixing-settling zone 6 in conduit 15 exits conduit 15 in conduit 17 and passes to catalyst regeneration zone 18. Superheated isoparaffin vapor is introduced into the catalyst regeneration zone in conduit 19. Catalyst regeneration 18 is operated at conditions selected to provide an isoparaffin stream which exits in conduit 14, a regenerated catalyst stream which exits in conduit 16 and a stream comprising tar and CBM which exits in conduit 20. The isoparaffin stream in conduit 14 passes to conduit 2, intermixing therein with isoparaffin from separation zone 8. Hydrogen fluoride in conduit 10 intermixes with the regenerated catalyst in conduit 16, and the resultant mixture passes to reaction zone 4 through conduit 3.

Figure 2:
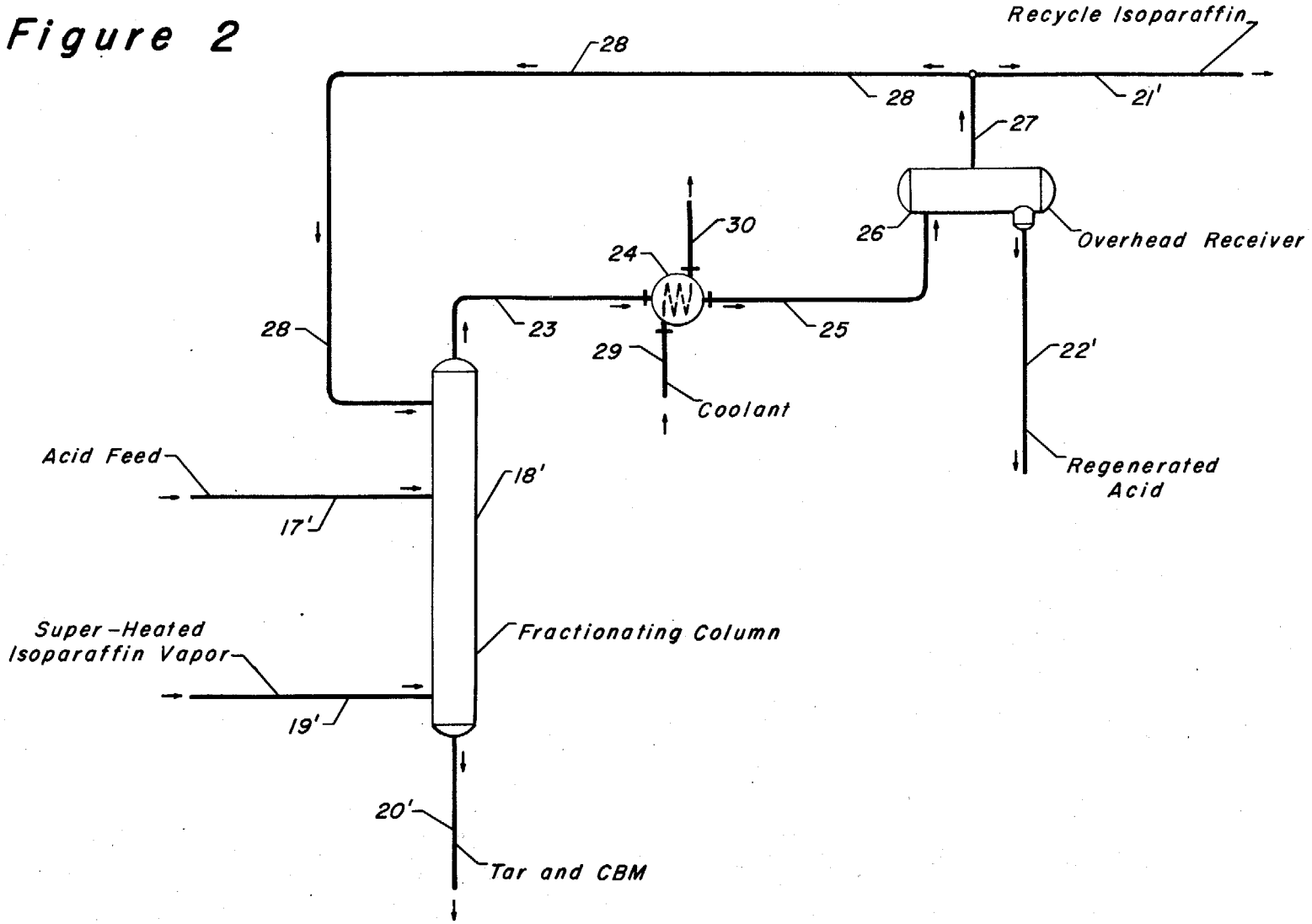
FIG. 2 is a schematic diagram of a catalyst regeneration zone, showing fractionating column 18′ and overhead receiver 26.

Referring now to FIG. 2, contaminated hydrogen fluoride catalyst, comprising hydrogen fluoride, water and heavy organic material, enters the regeneration process of our invention in conduit 17′; passing to fractionating column 18′. Superheated isoparaffin vapor enters fractionating column 18′ in conduit 19′. Hydrogen fluoride vapors and isoparaffin vapors exit fractionating column 18′ in conduit 23, are condensed in heat exchanger 24 and pass in conduit 25 to overhead receiver 26. A suitable coolant such as water or air enters exchanger 24 in conduit 29, absorbs the heat liberated by the condensing vapors and exits in conduit 30. In a preferred embodiment of our invention overhead receiver 26 is a horizontally disposed vessel having a boot which is situated at a place on the bottom of the vessel downstream of the inlet point of conduit 25 and which communicates with said vessel. The condensed overhead, which contains immiscible acid and isoparaffin phases must pass the boot in flowing through the receiver. The denser hydrogen fluoride phase falls into the boot, and the isoparaffin stream which exits overhead receiver 26 in conduit 27 is free from an acid phase. The hydrogen fluoride phase exits overhead receiver 26 in conduit 22′ and is referred to as regenerated acid because it is substantially anhydrous and substantially free from heavy organic material. The isoparaffin phase entering overhead receiver 26 in conduit 25 separates from the hydrogen fluoride phase and exits in conduit 27. A portion of the isoparaffin in conduit 27 exits in conduit 28, returning to the top of fractionating column 18′ as reflux. The remaining portion of isoparaffin in conduit 27 exits in conduit 21′ and is referred to as recycle isoparaffin because it is suitable for use as such in an alkylation process. Heavy organic material, referred to as tar, and an azeotropic mixture of water and hydrogen fluoride, referred to as CBM (constant boiling mixture), exit fractionating column 18′ in conduit 20′.

Referring again to FIG. 1, feed to an alkylation process unit commonly contains, as well as the olefin and isoparaffin components, normal paraffins of carbon content substantially equal to that of the olefin and isoparaffin components. Hence, a feed comprising propene and butene as the olefinic components and isobutane as the isoparaffinic one will ordinarily contain at least some propane and normal butane. The propane and butane exit the process unit in the hereinbefore described liquefied hydrocarbon vapor stream and in the hydrocarbon liquid stream respectively. Propane entering the process with the feed in conduit 1 will exit the process in conduit 9, passing to downstream fractionation facilities for recovery. Normal butane entering the process in conduit 1 exits in conduit 12 and passes to downstream treating facilities where trace amounts of organic fluorides and hydrogen fluoride may be removed as desired.

DETAILED DESCRIPTION OF THE INVENTION

In the hydrogen fluoride-catalyzed alkylation process of our invention, reactants combine to yield as a principal product a hydrocarbon of carbon content equal to the sum of the carbon atoms of the individual olefin and alkylatable reactants. Such hydrocarbon products are referred to as mono-alkylate since the alkylatable reactant is substituted with only one whole olefinic reactant. Monoalkylate is the most desirable alkylate product because of its exceptional octane and boiling point characteristics as compared to heavier alkylate, that having a carbon content greater than monoalkylate. This heavier alkylate is a result of undesirable reactions such as polymerization. When alkylation is performed in the presence of hydrogen fluoride, a strongly acidic catalyst, it is necesary to choose reaction conditions which favor alkylation rather than polymerization and other undesirable reactions, since acidic catalysts will also promote the undesirable ones. For simplicity, discussion will be limited to the polymerization reaction. Four major variables are important in minimizing polymerization: reaction temperature, excess of alkylatable isoparaffin reactant, the catalyst and catalyst composition. The process of this invention optimizes these four variables, however, in its essence it most concerns the variable of excess of alkylatable isoparaffin reactant.

When feed to an alkylation process unit comprises isoparaffin and olefin constituents, it is necessary to provide an excess of isoparaffin within the reaction by recycling unreacted isoparaffins from the reaction zone effluent back to the fresh feed prior to its introduction into the reaction zone. This excess of alkylatable reactant tends to maximize mono-alkylate production. It is essential that this recycle isoparaffin be thoroughly admixed and intermingled with the olefin-containing fresh feed before contact is effected with the acid catalyst phase. Therefore, the recycle isoparaffin must not contain hydrogen fluoride as a separate phase. For this reason conventional alkylation process designs have returned the hyrogen fluoride-isoparaffin admixture from the catalyst regeneration zone to the catalyst inlet of the reaction zone, without making use of the isoparaffin portion of the admixture to maximize monoalkylate production. Since this isoparaffin is not admixed with fresh feed prior to contact between the fresh feed and the acid phase it does not appreciably affect monoalkylate production. The isoparaffin merely consumes space within the reaction zone, and because it is of no beneficial use to the process, the energy consumed in circulating it is wasted. We have discovered that if the isoparaffin is separated from regenerated catalyst in the catalyst regeneration zone it can be utilized as recycle isoparaffin, provided that it does not contain hydrogen fluoride as a phase.

The feed to the catalyst regeneration zone of an isoparaffin-olefin alkylation process normally comes from the hydrogen fluoride phase of the mixer-settler. Such a hydrogen fluoride phase is referred to as contaminated catalyst since it contains water and heavy organic material. Isoparaffin vapors are commonly injected into the catalyst regeneration zone to aid in stripping out the acid catalyst. These isoparaffins exit the common catalyst regeneration zone with the regenerated acid and return to the reaction zone without being used as recycle isoparaffins. The resulting acid-isoparaffin admixture is generally about 80 weight percent isoparaffin. Our invention finds its greatest utility in putting these isoparaffins to more productive use.

In the embodiment of our invention shown in the attached FIG. 1, 3636 barrels per stream day (BPSD) of olefin-isoparaffin feed enter the process in conduit 1. This feed is of approximately the following composition, expressed in mole percent: propene, 20.0; propane, 8.6; butene 23.7; isobutane 42.2; normal butane, 5.5. The feed combines with 23,701 BPSD of recycle isoparaffin from conduit 2 of approximately the following composition, expressed in mole percent: propane, 13.5; isobutane, 80.0; normal butane, 5.0; isopentane, 1.0; $C_6$ and heavier, 0.5. This combined feed and recycle contact hydrogen fluoride in reaction zone 4 and pass to the bottom of mixing-settling zone 6. The mixing-settling zone of this example may be a vertically disposed, cylindrical vessel having a lower mixing section and an upper settling section. The mixing section preferably has flow restrictions placed therein, such as baffles, which maintain the reaction zone effluent in a dispersed state. The volume of the mixing section is selected to provide sufficient residence time for completion of reactions begun in the reaction zone. The settling section of the mixing-settling zone provides for repose of the catalyst - hydrocarbon dispersion so that phase separation can occur. Catalyst and hydrocarbon phases separate within the settling zone by virtue of their different densities. The settling section of this example may comprise an enclosed void space. The hydrocarbon phase exits mixing-settling zone 6 in conduit 7 and passes to separation zone 8. 2,755 BPSD of alkylate product exit separation zone 8 in conduit 13. 400 BPSD of hydrocarbon liquid exit separation zone 8 in conduit 12 and pass to downstream treating facilities. This hydrocarbon liquid is of approximately the following composition, expressed in mole percent isobutane, 5.0; normal butane, 92.5; isopentane, 2.0; hexane and heavier, 0.5. 1,687 BPSD of a liquefied hydrocarbon vapor exit separation zone 8 in conduit 9, passing to downstream fractionation facilities. This liquefied hydrocarbon vapor is of approximately the following composition, expressed in mole percent: propane, 24.6; isobutane, 71.6; normal butane, 3.4; isopentane, 0.4, 2,320 pounds per hour of hydrogen fluoride exit the separation zone in conduit 10 and return to reaction zone 4, 182,554 Pounds per hour of recycle isoparaffin exit separation zone 8 in conduit 11 and pass to feed conduit 1 through conduit 2. The separation zone may be one or more plate or packed fractionation towers.

A hydrogen fluoride phase exits mixing-settling zone 6 in conduit 15. This phase comprises hydrogen fluoride, water and heavy organic material and is referred to as contaminated catalyst. The contaminated catalyst is separated into two portions. A first portion returns to reaction zone 4 through conduit 3, and the remaining portion passes to catalyst regeneration zone 18 through conduit 17. Referring again to the regeneration zone shown in FIG. 2, 2,120 pounds per hour of contaminated catalyst enter the middle portion of fractionating column 18' in conduit 17'. 7,840 Pounds per hour of superheated isoparaffin vapor enter the lower portion of the fractionating column in conduit 19' and pass upwardly therethrough, counter-currently contacting the contaminated catalyst and stripping the hydrogen fluoride from it. 12,566 Pounds per hour of overhead vapors leave fractionating column 18' in conduit 23, passing to condenser 24. The vapors are condensed and the resulting liquid passes to overhead receiver 26 in conduit 25. The overhead receiver provides a period of repose for the condensed overhead vapors so that the isoparaffin and hydrogen fluoride phases may separate. Overhead receiver 26 is provided with a boot, or lower appendage, which provides a catchment for the hydrogen fluoride phase from which 2,086 pounds per hour of hydrogen fluoride, substantially free from water and heavy organic material, are withdrawn. This hydrogen fluoride phase is returned to reaction zone 4 as regenerated catalyst. 10,450 Pounds per hour of isoparaffins, substantially free from hydrogen fluoride as a phase, exit overhead condenser 26 in conduit 27 and are separated into two portions. A first portion of 2,610 pounds per hour returns to the fractionating column as reflux in conduit 28. The remaining portion of the isoparaffins, 7,840 pounds per hour, exits conduit 27 in conduit 21'. It is suitable for mixing with alkylation process feed and will improve the alkylation process by increasing mono-alkylate production. Cooling water enters condenser 24 in conduit 2, absorbs heat liberated by condensing vapors and exits in conduit 30. 34 Pounds per hour of an admixture of heavy organic material and an azeotropic mixture of hydrogen fluoride and water (CBM) is withdrawn from fractionating column 18' in conduit 20'. In a preferred embodiment of our invention the fractionating column is a conventional plate or packed tower having 5 to 15 contact stages.

Our invention is not restricted to the conditions of the aforementioned example. A suitable alkylatable reactant may be a paraffinic hydrocarbon having a tertiary carbon atom, such as 2-methylbutane, 2-methylpentane, etc. Other useful alkylatable reactants include benzene, toluene, xylene, naphthenes, phenols, cresols, amines and the like. The olefin reactants which suitably may be used in our invention include $C_3 - C_{20}$ olefinic hydrocarbons, alkyl halides, alcohols, alkyl sulfates, alkyl phosphates, etc. Hydrogen fluoride is used as the alkylation catalyst. A preferred hydrogen fluoride catalyst contains from 80–90 percent hydrogen fluoride, less than 2 percent water and soluble organic material as the balance of 100 percent. Alkylation reaction conditions to be maintained within the reaction zone include a temperature from about 0° F. to about 150° F., and a pressure of about 1 atmosphere to about 40 atmospheres. A preferred range of temperature is from about 30° F. to about 100° F. Pressure is not a significant variable with respect to product quality, provided that it is sufficient to keep all hydrocarbon in the liquid state. The volumetric ratio of acid catalyst to hydrocarbon within the reaction zone is maintained within the range of 0.5:1 to 2:1. At some point below 0.5:1 excess polymer forms which contaminates the alkylate product. There appears to be no alkylate yield or quality improvement in increasing this ratio above 2:1. The contact time in the alkylation reaction zone is typically less than 5 minutes and preferably from about 10 to about 60 seconds. It is desirable to maintain a high mole ratio of isoparaffin or aromatic present to the olefin present in order to produce high quality monoalkylate. A broad range of this ratio is from about 7:1 to about 20:1 with a preferred operating range being from about 8:1 to 16:1. The residence time in the mixing-settling zone is preferably from about 100 seconds to about 1200 seconds. Operating conditions in the separation zone are selected according to the type of reactants being charged to the process. A preferred range of pressure in the fractionating column of the catalyst regeneration zone is from 140 to 300 psig.

We claim as our invention:

1. An alkylation process comprising:

(a) contacting a feed comprising an olefin and an isoparaffin with hydrogen fluoride alkylation catalyst at alkylation reaction conditions in a reaction zone;

(b) separating a reaction zone effluent into a hydrocarbon phase and a catalyst phase;

(c) returning a first portion of said catalyst phase to said reaction zone;

(d) passing a second portion of said catalyst phase to a catalyst regeneration zone to remove tar and constant boiling mixture of water and hydrogen fluoride from said [ acid ] *catalyst* phase;

(e) passing said hydrocarbon phase to a separation zone to separate unreacted isoparaffin and to withdraw an alkylate product;

(f) mixing said unreacted isoparaffin from step (e) with said feed prior to introducing said feed into said reaction zone;

(g) separating a mixture of regenerated acid and isoparaffin from said catalyst regeneration zone;

(h) condensing said mixture into regenerated acid and isoparaffin *substantially free of hydrogen fluoride*; and, (i) recycling said regenerated acid to said reaction zone [ in ] *of* step (a) and mixing said isoparaffin from step (h) with said feed [ in step (a). ] *prior to introducing said feed into said reaction zone.*

[ 2. The process of claim 1 further characterized in that said isoparaffin in step (h) is substantially free of a hydrogen fluoride. ]

3. An alkylation process comprising:

(a) contacting a feed comprising an olefin and an isoparaffin with hydrogen fluoride alkylation catalyst at alkylation reaction conditions in a reaction zone;

(b) separating a reaction zone effluent into a hydrocarbon phase and a catalyst phase;

(c) returning a first portion of said catalyst phase to said reaction zone;

(d) passing a second portion of said catalyst phase to a catalyst regeneration zone to remove tar and constant boiling mixture of water and hydrogen fluoride from said [ acid ] *catalyst phase;*

(e) passing said hydrocarbon phase to a separation zone to separate unreacted isoparaffin and to withdraw an alkylate product;

(f) mixing said unreacted isoparaffin from step (e) with said feed prior to introducing said feed into said reaction zone;

(g) separating regenerated acid catalyst from said catalyst regeneration zone and recycling said regenerated acid catalyst to said reaction zone [ in ] *of* step (a); and, (h) separating isoparaffin *substantially free of hydrogen fluoride* from *said* catalyst regeneration zone and mixing said separated isoparaffin with said feed [ in step (a). ] *prior to introducing said feed into said reaction zone.*

[ 4. The process of claim 3 further characterized in that said feed comprises isobutane and an olefin having 3 to 4 carbon atoms per molecule. ]

[ 5. The process of claim 3 further characterized in that said hydrogen fluoride alkylation catalyst is maintained between about 80 and 90 weight percent hydrogen fluoride. ]

* * * * *